United States Patent [19]

Geysen

[11] Patent Number: 5,194,392
[45] Date of Patent: Mar. 16, 1993

[54] METHOD OF DETERMINING MIMOTOPES

[75] Inventor: Hendrik M. Geysen, Knoxfield, Australia

[73] Assignee: Commonwealth Serum Labortories, Commission, Australia

[21] Appl. No.: 541,169

[22] Filed: Jun. 21, 1990

Related U.S. Application Data

[63] Continuation of Ser. No. 864,341, May 22, 1986, abandoned.

[30] Foreign Application Priority Data

Jul. 24, 1984 [AU] Australia ................ PG6188/84

[51] Int. Cl.⁵ ................ G01N 33/543; G01N 33/531; C07K 1/04
[52] U.S. Cl. ................ 436/518; 435/7.1; 435/7.92; 436/531; 436/532; 436/543; 530/333; 530/334; 530/806; 530/815; 530/826
[58] Field of Search ............ 435/7.1, 7.92; 436/518, 436/531, 532, 543; 530/806, 815, 826, 333, 334

[56] References Cited

U.S. PATENT DOCUMENTS

| | | | |
|---|---|---|---|
| 4,415,491 | 11/1983 | Vyas | 530/806 |
| 4,493,795 | 1/1985 | Nestor et al. | 530/326 |
| 4,554,101 | 11/1985 | Hopp | 436/543 |
| 4,578,217 | 3/1986 | Vnek et al. | 530/806 |
| 4,591,552 | 5/1986 | Neurath | 530/806 |

FOREIGN PATENT DOCUMENTS

84/03564 9/1984 World Int. Prop. O.

OTHER PUBLICATIONS

Lerner, Scientific American, vol. 248, No. 2, Feb. 1983, pp. 66-74.

Hopp. et al, Proc. Natl. Acad. Sci. USA, vol. 78, No. 6, Jun. 1981, pp. 3824-3828.

Smith, J. A., Hurrell, J. G. R. and Leach, S. J., "A Novel Method for Delineating Antigenic determinants: Peptide Synthesis and Radioimmunassy Using the Same Solid Support", Immunochemistry, 24; 565-568, 1977.

Houghten, R. A., "General Method for the Rapid Solid-phase Synthesis of large Numbers of Peptides: Specificity of Antigen-antibody Interaction at the Level of Individual Amino Acids", Proc. Nat'l. Acad. Sci, USA, 82: 5131-5135, 1985.

Kent, S., Neurath, A. R., Aebersold, R., Parker, K. & Strick, N., "Epitope scanning-Strategies for Determining the Precise Location of Continuous Epitopes Applied to the pre-S Region of HBV", Cold Spring Harbor Symposium, Modern Approaches to Vaccines, Sep. 1985.

Primary Examiner—Esther L. Kepplinger
Assistant Examiner—Toni R. Scheiner
Attorney, Agent, or Firm—Sughrue, Mion, Zinn, Macpeak & Seas

[57] ABSTRACT

A method of detecting or determining the sequence of monomers which is a topological equivalent of the epitope which is complementary to a particular paratope of an antibody of interest, comprises the steps of: 1) synthesizing a plurality of catamer preparations; each of the catamer preparations consisting of a plurality of catamers in which the composition at one or more designated positions in each catamer is known, and the composition at the remaining positions is randomly made up from members of a defined set of monomers; and the plurality of catamer preparations comprises preparations in which the composition at the designated positions is systematically varied to contain members from a defined set of monomers; 2) contacting each of the plurality of catamer preparations with the antibody of interest; and 3) detecting or determining the presence or absence of binding between each of the plurality of catamer preparations and the given antibody to indicate a partial sequence of the mimotopes for the paratope of the given antibody.

6 Claims, 6 Drawing Sheets

METHOD OF DETERMINING MIMOTOPES

This is Continuation of application No. 06/864,341 filed May 22, 1986, now abandoned.

This invention relates to a method of detecting or determining a sequence of monomer molecules which corresponds to an epitope on an antigen, or which has the equivalent molecular topology to that epitope.

As used throughout this specification, the terms listed below have the following meanings:

epitope: the specific surface of an antigen molecule which is delineated by the area of interaction with an antibody molecule.

catamer: a polymer molecule which has a precisely defined sequence and which is formed by the condensation of a precise number of small molecules. Note that this term includes molecules in which different types of condensation reactions are used to join the small molecules. A number prefixed to the word 'catamer' indicates that the catamer is formed by the condensation of the indicated number of small molecules, for example, 8-catamer means that the catamer is made up from eight small molecules. Examples of catamers include any given peptide, and any given oligo-saccharide.

monomer: a member of the set of small molecules which can be condensed together to form a catamer. The set of monomers includes but is not restricted to, for example, the set of common L-amino acids, the set of D-amino acids, the set of synthetic amino acids, the set of nucleotides, and the set of pentoses and hexoses.

peptide: a catamer in which the small molecules are alpha-amino acids which are joined together through peptide bonds. In the context of this specification it should be appreciated that the amino acids may be the L-optical isomer or the D-optical isomer.

mimotope: catamer which in at least one of its conformations has a surface region with the equivalent molecular topology to the epitope of which it is a mimic.

complementary: refers to the matching together of the reacting surfaces of an antibody paratope and its particular epitope. These surfaces must match during the binding of an antibody paratope with its epitope. Thus, the paratope and its epitope can be described as complementary, and furthermore, the contact surface characteristics are complementary to each other.

paratope: the combining site of an antibody which is complementary to a particular epitope.

It is already well known that:
1. an antigen is a macromolecule such as a protein or polysaccharide which is usually, but not necessarily, foreign to a human or animal and when introduced into the human or animal body, stimulates either a humoral or cellular immune response, or both;
2. the specific region of the antigen to which antibodies bind is known as the epitope;
3. there may be more than one epitope on an antigen molecule;
4. the overall humoral response of the body to an antigen is to produce antibodies against the various epitopes of the antigen; each of the individual antibodies is a monoclonal antibody and by definition is produced from a group of cells which come from the multiplication and differentiation of a single progenitor B-cell;
5. the paratope of an antibody molecule is defined as the molecular surface of the antibody combining site which is the contact surface between epitope and the antibody;
6. there may be produced against a given epitope of the antigen more than one antibody which differ in their paratopes; each paratope can be characterised by its specificity for the complementary epitope; and
7. antibodies produced in response to a challenge by antigen can be further characterised in that some may neutralize directly by binding with the antigen; others may form aggregates which can be dealt with by the macrophage system; and yet others may fail to exhibit any measurable biological effects.

It is a primary object of the present invention to detect or determine the one or more short sequences of monomers which equate with an epitope of an antigen, such that these sequences can combine with the same antibody as the epitope. These catamers would be the mimotopes of the epitope. This information is invaluable in the design of synthetic catamer vaccines against diseases and for the design of very specific diagnostic and therapeutic agents.

The most usual group of small molecules which may be condensed together to form a catamer is the group of alpha-amino acids. However, other molecules which are consistent with the chemistry chosen may be used. For example, beta-amino acids may be used with advantage to add an extra -C- bond spacer at precisely controlled positions in the catamer.

According to the present invention there is provided a method of detecting or determining the sequence of monomers which is a topological equivalent of the epitope which is complementary to a particular paratope of an antibody of interest, the method comprising the steps of:
1. synthesizing a plurality of catamer preparations; each of said catamer preparations consisting of a plurality of catamers in which the composition at one or more designated positions in each catamer is known, and the composition at the remaining positions is randomly made up from members of a defined set of monomers; and said plurality of catamer preparations comprising preparations in which the composition at the designated positions is systematically varied to contain members from a defined set of monomers;

2. contacting each of said plurality of catamer preparations with the antibody of interest; and
3. detecting or determining the presence or absence of binding between each of said plurality of catamer preparations and said given antibody to indicate a partial sequence of the mimotopes for the paratope of the said given antibody.

Preferably, the method also comprises the further steps of:
4. synthesizing a further plurality of catamer preparations as described above, each of said further plurality of catamer preparations having one or more additional positions in each catamer as a designated position; and
5. repeating steps 2 and 3 above in respect of said further plurality of catamer preparations.

The procedures of steps 4. and 5. may be repeated until all positions in each catamer preparation have been designated; and all deduced mimotopes may then be synthesised to determine from their relative ability to react with the antibody of interest which are the better mimotopes for the epitope corresponding to this given antibody.

The method of the present invention is based on the realisation that a given antibody will specifically react with a catamer which is the mimotope of the epitope to which the antibody is directed. It further relies on the knowledge that modern techniques of immunology allow the detection of reactions between an antibody and its epitope when both are present in very small amounts. Binding has been detected when an antibody and its epitope are present in amounts of about 1 pmole. Thus, if an antibody is presented with a mixture of catamers, amongst which is a mimotope to its epitope then it will be seen to react with the mixture, binding specifically to the mimotope. The identity of mimotopes is deduced from the known monomer composition at the designated positions of reacting catamer preparations. A complete mimotope would be expected to be some combination of the reacting components deduced in this way.

It will be apparent that the method of this invention requires no previous information about the nature of the antigen and in particular it requires no foreknowledge of the sequence of monomers which make up the antigen. In fact, it is not necessary for the application of this invention to know the source or the identity of the antigen to which the antibody is directed. Furthermore, this invention makes no assumptions about the epitope which stimulated the production of the particular antibody. This method will identify mimotopes of discontinuous as well as continuous epitopes. Because of the very nature of the method of the invention it will be appreciated that it applies to any antigen, which in part or in total is non-proteinaceous, whose epitopes can be mimicked by a suitable catamer. Mimotopes may or may not be made from members of the same set of monomers which make up the antigen.

Preferably the method of the present invention is carried out by screening a plurality of synthesized catamer preparations against an antibody of interest. Ideally the antibody will be a monoclonal antibody which can be prepared by any of the usual methods. Polyclonal antiserum from humans and animals may be used if a source of monoclonal antibody is not available, however, analysis of the resulting data may be complicated because the reactions observed could be from more than one monoclonal antibody. When using polyclonal antiserum it may be necessary to reduce the antibody diversity by using techniques well known to those skilled in the art, for example iso-electric focusing, HPLC-based chromatography or affinity chromatography.

Current indications suggest that an epitope can be mimicked by a catamer which is about eight monomers in length when the monomers come from the set of alpha amino acids. The ability of the 8-catamer to be the mimotope of the epitope is not critically dependent on every position having a particular monomer. It is to be understood, however, that the present invention is not restricted to sequences formed from eight monomers.

The plurality of catamer preparations required to be synthesized in the application of this invention may be prepared by any of the known methods of catamer synthesis. The preferred method when the monomers are amino acids is to use the solid phase technique described in Australian Patent Specification No. 25429/84, whereby each mixture of catamers is synthesized on a polyethylene support.

The following is a detailed description of one embodiment of the present invention:

A. Synthesis of a plurality of catamer preparations

As noted above, the preferred method of applying this invention is to synthesize the catamers on a solid support. In this embodiment, the plurality of catamers will all have the general formula $Y-X-X-D_2-D_1-X-X-X-X-$[solid support], where 'X' represents a member of a set of monomers. Ideally, each catamer preparation should include catamers in which each of the 'X' positions in the catamer formula represents a member of the set of monomers such that each member of the set is present in the catamer preparation in approximately equimolar amounts. Note that the same set of monomers need not be used at each 'X' position. 'Y' in the general formula is an end group of the catamer and may be, but is not restricted to, for example a hydrogen atom or an acetyl group. $D_1$ and $D_2$ represent designated positions occupied by monomers which are known and constant in each catamer preparation synthesized; but which are altered systematically between catamer preparations. Note that the same set of monomers need not be used at each designated position It should also be noted that when the catamers are synthesized from amino acids the catamers may be coupled to the solid support through their —COOH ends, or through their amine ends.

If i is the number of members in the set of monomers to be coupled in the $D_1$ position and j is the number of members in the set of monomers to be coupled in the $D_2$ position then a total of i.j different catamer preparations will be synthesized.

In the present embodiment, the support rods are prepared so that the monomers can be coupled to them. The rods are then exposed to the reaction mixture containing each member of the set of monomers being considered. This will couple monomers at the first 'X' position. This process is repeated thrice to give the catamer Z—X—X—X—X—[solid support] where 'Z' is the protective group appropriate to the set of monomers being considered; examples of 'Z' where the monomers are amino acids include the BOC and Fmoc groups. Up to this stage in the performance of the method all rods have been treated in an identical manner.

For the coupling at the $D_1$ position each rod will be treated with a reaction mixture which contains only a single monomer such as a protected amino acid or the like. In the $D_1$ position each of the i monomers will be coupled to j rods. For the coupling at the $D_2$ position each rod is again treated with a reaction mixture containing only a single monomer such as a protected amino acid or the like. Each of the j rods which has a particular monomer in the $D_1$ position will have a different monomer coupled at the $D_2$ position. In this way every combination of the members of the set(s) of monomers will be found in the i.j rods. Coupling of monomers in the remaining 'X' positions is identical to the coupling in the 'X' positions closer to the solid support.

After synthesis of the plurality of catamer preparations any side-chain protective groups are removed from the catamer preparations using the usual techniques and the rod-coupled catamers are washed.

It has been found to be a preferred embodiment of the invention to synthesize more than one set of pluralities of catamer preparations to aid in the analysis of data. Thus, as well as synthesizing catamers with the general formula Y—X—X—$D_2$—$D_1$—X—X—X—X—[solid support]

as described above, additional sets of catamers may be prepared with the general formulae Y—X—X—$D_2$—X—$D_1$—X—X—X—[solid support]

and

Y—X—$D_2$—X—X—$D_1$—X—X—X—[solid support].

Note that other general formulae may be selected for the syntheses of other sets of catamer preparations.

B. Testing of the catamer preparations

The plurality of catamer preparations prepared as in A above are then contacted with the particular antibody of interest. The reaction between antibody and components of the catamer preparations can then be detected by any of the usual methods, for example Radioimmunoassay (RIA). However, the preferred method of detection of the presence of antibody-mimotope binding is to use the well-known enzyme-linked immunosorbent assay (ELISA).

At the end of each assay antibodies can be removed from the catamer preparations by, for example, washing with a solution of 8M urea, 0.1% 2-mercaptoethanol and 0.1% sodium dodecylsulphate followed by several washes in phosphate buffered saline. In this way the plurality of catamer preparations may be used for testing with many other antibodies.

C. Analysis of data.

In the testing of the catamer preparations with antibody it will be found that certain rods will show detectable binding with the antibody. The catamer preparation coupled to such a reacting rod contains a defined combination of the members of the set(s) of monomers in positions $D_1$ and $D_2$. This combination of monomers is likely to form part of the catamer which makes up a mimotope for the epitope which is complementary to the antibody. Further analysis of the data can be carried out in a number of ways. These include:

1. combining and permutating these reacting monomers to create a list of catamers which may include one or more mimotopes for the epitope; each catamer in this list could be regarded as a possible mimotope;
2. taking the most suitable candidates from the list of reacting combinations of monomers (but not necessarily those giving the highest antibody binding activity) and further synthesizing sets of catamer preparations in which the known reacting combination of monomers is held constant and the monomers at other positions of the catamers are varied systematically; thus in the example above, a suitable set of such catamer preparations would include catamers with the formulae Y—X—$D_3$—$D_2$—$D_1$—X—X—X—X—[solid support]

and

Y—X—X—$D_2$—$D_1$—$D_4$—X—X—X—[solid support], where $D_1$ and $D_2$ constitute the reacting combination of monomers and $D_3$ and $D_4$ are other designated positions where each of the members of the set of monomers is systematically varied; and
3. combining the results from more than one of the sets of plurality of catamer preparations and decoding to produce a single sequence of monomers, or possibly a very small number of such sequences which may mimic the epitope of interest; this is because, using the embodiment given above, the reacting combinations of monomers when they are adjacent to each other, the reacting combinations of monomers when they are separated by one position and finally the reacting combinations of monomers which are separated by two positions, are all known; these data may be easily decoded to yield the sequence of the mimotope; this approach will be of greatest benefit when the antibody used to test the plurality of catamer preparations is a monoclonal antibody.

D. Synthesis of selected mimotopes

The selected mimotopes can then be synthesized using similar methods to those described in Australian Patent Specification No. 25429/84. After the selected catamers have been synthesized they are reacted with the antibody of interest. It is then simple to select the catamer which binds most strongly with the antibody As a final check that this catamer is the best mimotope of the epitope, the sequence of the catamer may be used as the parent sequence of a replacement net as described in Australian Patent Specification No. 25428/84.

In Examples 1, 2 and 3 given below, the defined set of monomers is the set of the common L-alpha amino acids. This set of monomers is used for both the designated positions and the random positions (positions '$D_1$', '$D_2$' and 'X' as used in the general formulae above). Furthermore, in these examples, the end group of the catamers (the 'Y' group) was the acetyl moiety.

EXAMPLE 1

A plurality of 8-catamer preparations was synthesized with the general formula

Acetyl—NH—X—X—D₂—D₁—X—X—X—X—[-solid support]

where 'X' is a member of the set of 20 common L-alpha amino acids, such that each member of the set is present at the 'X' position in the catamer preparations in approximately equi-molar amounts; both designated positions, $D_1$ and $D_2$ are members of the same set of monomers; and '—NH—' represents the terminal amine group of the catamer. The 8-catamer preparations were synthesized on a solid polymer pin or rod as described in general in Australian Patent Specification No. 25429/84, using the BOC group as protection for the L-alpha amino acids during synthesis.

Members of the set of common L-amino acids were coupled in the 'X' positions in the following way:

1. A mixture of amino acids was dissolved in 102 ml of Dimethylformamide (DMF). The mixture consisted of:

| | |
|---|---|
| BOC—L—Alanine | 32 mg |
| BOC—Methoxybenzyl-L—Cysteine | 100 mg |
| BOC—Benzyl-L—Aspartic acid | 90 mg |
| BOC—Benzyl-L—Glutamic acid | 96 mg |
| BOC—L—Phenylalanine | 61 mg |
| BOC—L—Glycine | 27 mg |
| BOC—Tosyl-L—Histidine | 142 mg |
| BOC—L—Isoleucine.½ H₂O | 51 mg |
| BOC—Carbobenzoxy-L—Lysine | 124 mg |
| BOC—L—Leucine.H₂O | 55 mg |
| BOC—L—Methionine | 54 mg |
| BOC—L—Asparagine | 47 mg |
| BOC—L—Proline | 42 mg |
| BOC—L—Glutamine | 53 mg |
| BOC—Tosyl-L—Arginine.H₂O | 167 mg |
| BOC—Benzyl-L—Serine | 76 mg |
| BOC—Benzyl-L—Threonine | 83 mg |
| BOC—L—Valine | 42 mg |
| BOC—L—Tryptophan | 78 mg |
| BOC—Benzyl-L -Tyrosine | 116 mg |

2. A solution of 1310 mg of 1-Hydroxybenzotriazole (HOBT) was made in 34 ml of DMF.
3. A solution of 1150 mg of N,N'-Dicyclohexylcarbodiimide (DCC) was made in 34 ml of DMF.
4. Before use, the solution of HOBT was added to the solution of amino acids and mixed. Then the solution of DCC was added and mixed. The catamer or linking molecule already on the solid support was then reacted with the resulting mixture.

Individual L-amino acids were coupled in the $D_1$ and $D_2$ positions by the method described in Australian Patent Specification No. 25429/84. This resulted in the synthesis of 400 catamer preparations, comprising all possible pairings of the 20 common amino acids at the $D_1$ and $D_2$ positions.

The plurality of 8-catamer preparations were tested against a monoclonal antibody by ELISA. This monoclonal antibody was prepared against Foot-and-Mouth Disease Virus (FMDV) subtype $A_{10}$ using techniques well known to those skilled in the art. In performing the ELISA assay support-coupled peptides were incubated in a precoat solution of 1% ovalbumin/1% bovine serum albumin/0.1% Tween 20 in phosphate buffered saline (PBS) for 1 hr at 25° C. to block non-specific absorption of antibodies. Overnight incubation at 4° C. in a suitable dilution of monoclonal antibody in precoat solution was followed by three washes in 0.05% Tween 20/PBS. Reaction for 1 hr at 25° C. with goat anti-mouse IgG conjugated to horseradish peroxidase, diluted in the precoat solution, was again followed by extensive washing with PBS/Tween to remove excess conjugate. The presence of antibody was detected by reaction for 45 min with a freshly prepared enzyme substrate solution (40mg of o-phenylenediamine and 18 μl of "120 vol." hydrogen peroxide in 100 ml of phosphate/citrate buffer, pH 5.0), and the colour produced determined at 450 nm.

FIG. 1 shows the result of testing the 8-catamer preparations with this antibody. In FIG. 1, each group of twenty lines represents the response in an ELISA in units of absorbancy of the colour developed when measured at 450 nm. Each member of the group of twenty lines has a common amino acid in the '$D_1$' position which is given in single-letter code immediately below each group. Each member of a group of twenty lines represents a different amino acid in the '$D_2$' position—these are in alphabetical order of their single-letter code. The results are summarised in Table 1. (In Table 1, and throughout the remainder of the Examples, the single letter code for amino acids will be used.)

TABLE 1

Antibody binding activities of the 8-catamer preparations mixtures Ac-X—X—$D_2$—$D_1$—X—X—X—X—$S_s$.

| Peptide Mixture | Extinction $E_{415}$ |
|---|---|
| Ac-X—X—M—H—X—X—X—X—$S_s$ | 0.624 |
| Ac-X—X—M—K—X—X—X—X—$S_s$ | 0.582 |
| Ac-X—X—K—K—X—X—X—X—$S_s$ | 0.537 |
| Ac-X—X—K—H—X—X—X—X—$S_s$ | 0.510 |
| Ac-X—X—Q—H—X—X—X—X—$S_s$ | 0.488 |
| Ac-X—X—H—H—X—X—X—X—$S_s$ | 0.486 |
| Ac-X—X—Q—N—X—X—X—X—$S_s$ | 0.460 |
| Ac-X—X—W—M—X—X—X—X—$S_s$ | 0.448 |
| Ac-X—X—K—N—X—X—X—X—$S_s$ | 0.431 |
| Ac-X—X—H—K—X—X—X—X—$S_s$ | 0.417 |

Mean extinction of the lower 200 values was 0.202 (Standard deviation 0.021).
Ac means the acetyl moiety.
$S_s$ means [solid support].

It will be seen that the antibody reacts strongly with a number of 8-catamer preparations. In order of strength of reaction, these include 8-catamer preparations in which the designated positions (—$D_2$—$D_1$—) are —M—H—, —M—K—, —K—K—, —K—H—, —Q—H— and —H—H—.

Two further pluralities of 8-catamer preparations where synthesized. These had the formulae Acetyl—NH—X—$D_3$—M—K—X—X—X—X—[-solid support]

and

Acetyl—NH—X—X—M—K—$D_4$—X—X—X—[-solid support]

where 'M' means a methionine residue, 'K' means a lysine residue and '$D_3$' and '$D_4$' are the new designated position for these series of syntheses; other terms in the formulae are as used previously.

These 8-catamer preparations were tested against the monoclonal antibody against FMDV $A_{10}$. FIGS. 2A and 2B show the results of ELISA testing with the monoclonal antibody used to produce the results shown in FIG. 1. FIG. 2A represents 8-catamer preparations with the general formula Acetyl—NH—X—$D_3$—M—K—X—X—X—X—[-solid support].

FIG. 2B represents 8-catamer preparations with the general formula

Acetyl—NH—X—X—M—K—D$_4$—X—X—X—[-solid support].

Figure 2A:
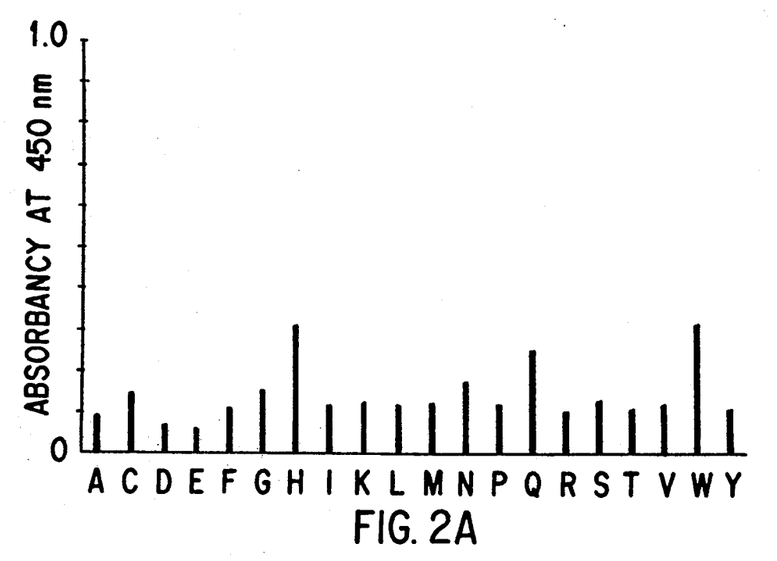
FIGS. 2A and 2B show the results of ELISA testing of 8-catamer preparations with monoclonal antibodies against FMDV.
Figure 2B:
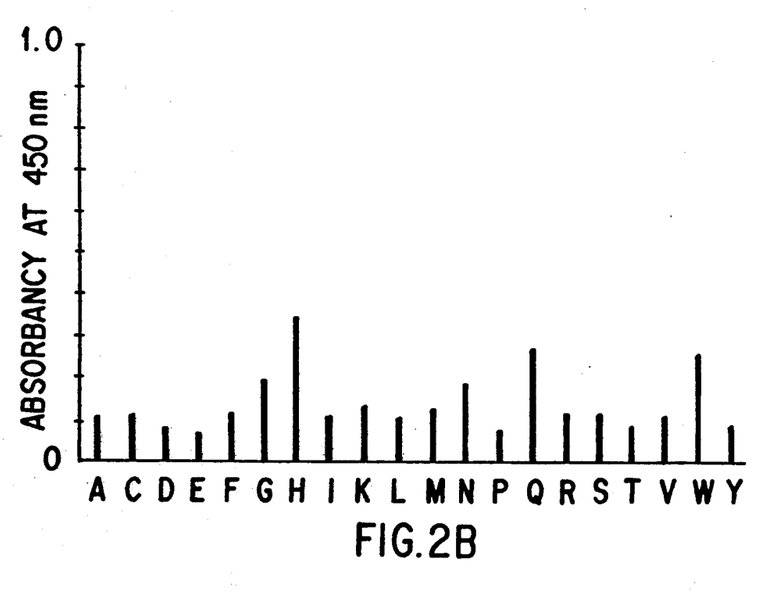

In both figures the amino acid in the '—D$_3$—' or '—D$_4$—' position is given below each line which represents the absorbancy of the colour developed when measured at 450 nm. The results are summarised in Table 2. Antibody binding activities are shown relative to the 8-catamer preparations containing the dfined amino acid pair M-K for all the 8-catamer preparations giving a value greater than 1.1. Also shown is the value found for the reverse pair K-M.

TABLE 2

Relative antibody binding activities of 8-catamer preparations containing three defined amino acids.

| Amino-terminal extension | | Carboxyl-terminal extension | |
|---|---|---|---|
| Sequence | Activity | Sequence | Activity |
| Ac-X—H—M—K—X—X—X—X—S$_s$ | 2.54 | Ac-X—X—M—K—H—X—X—X—S$_s$ | 2.85 |
| Ac-X—W—M—K—X—X—X—X—S$_s$ | 2.50 | Ac-X—X—M—K—Q—X—X—X—S$_s$ | 2.20 |
| Ac-X—Q—M—K—X—X—X—X—S$_s$ | 1.69 | Ac-X—X—M—K—W—X—X—X—S$_s$ | 1.97 |
| Ac-X—N—M—K—X—X—X—X—S$_s$ | 1.27 | Ac-X—X—M—K—G—X—X—X—S$_s$ | 1.41 |
| Ac-X—G—M—K—X—X—X—X—S$_s$ | 1.14 | Ac-X—X—M—K—N—X—X—X—S$_s$ | 1.26 |
| Ac-X—C—M—K—X—X—X—X—S$_s$ | 1.11 | | |
| Control sequences | M—K | 1.00 ($E_{450}$ = 0.14) | |
| | K—M | 0.97 | |
| Test background $E_{450}$ = 0.08. | | | |

It will be seen that the 8-catamer preparations which gave the greatest reactions with the monoclonal antibody had the following sequences in the designated positions: —H—M—K—, —W—M—K—, and —Q—M—K— in FIG. 2A; and —M—K—H—, —M—K—Q and —M—K—W— in FIG. 2B.

Incorporation of histidine at either side of the M-K defined pair resulted in the greatest antibody binding activity. However histidine at the amino terminal side was not significantly better than tryptophan, and the defined sequence W—M—K—H was selected for further evaluation.

The validity of proceeding with the defined sequence W—M—K—H, predicted to be optimal by combining the individual preferred extensions to the pair M-K, was tested. Catamer preparations based on the parent sequence of Acetyl—NH—X—W—M—K—H—X—X—X—S$_s$[solid support] were synthesized, in which at each of the four defined positions all 19 alternative amino acids were substituted, one at a time. Testing of this set of catamer preparations for binding activity with the test monoclonal antibody (MAb) showed Q—M—R-H to be the preferred sequence for extension ($E_{450}$ obtained were; Ac—X—W—M—K—H—X—X—X—S$_s$=0.69, Ac—X—Q—M—K—H—X—X—X—S$_s$=1.47, and Ac—X—W—M—R—H—X—X—X—S$_s$=1.11, test background was 0.2). The preference for glutamine at the amino-terminal side of the defined sequence M-K-H rather than tryptophan as had been determined for the pair M-K, demonstrates the interdependence of individually determined optima.

8-Catamer preparations with the general formulae

Acetyl—NH—D$_5$—Q—M—R—H—X—X—X— [solid support] and

Acetyl—NH—X—Q—M—R—H—D$_6$—X—X— [solid support]

were synthesized. The preparations with the highest antibody-binding activity were those with D$_5$=tryptophan and D$_6$=serine, which suggests that W—Q—M—R—H—S is the optimum sequence. No significant improvement in antibody binding activity was achieved by defining further amino acids to either end of this sequence. Assessment of the set of peptides comprising all the single amino acid substitutions of this sequence, synthesized as hexapeptides, confirmed that W—Q—M—R—H—S was close to the optimum hexapeptide. Some increase in antibody binding activity was shown when glycine replaced arginine in the peptide to give the sequence W—Q—M—G—H—S.

In order to confirm the specificity of the antibody-binding reaction of the determined group of related peptides for the test MAb, the titre of the test MAb for a number of the peptides was compared with those of a MAb to Sperm whale myoglobin or hepatitis A (Table 3). The specificity of the antibody-binding reaction is clearly for the test MAb, the antibody used to determine the sequence of those peptides.

TABLE 3

Specificity of Test MAb for W—Q—M—G—H—S related peptides.

| | Titre | | |
|---|---|---|---|
| Peptide | Test MAb | anti-hepatitis A | anti-myoglobin |
| Ac-X—X—M—K—X—X—S$_s$ | 2,000 | <200 | <200 |
| Ac-X—W—M—K—X—X—S$_s$ | 14,000 | <200 | 1,600 |
| Ac-X—X—M—K—H—X—S$_s$ | 17,000 | <200 | <200 |
| Ac-X—W—M—K—H—X—S$_s$ | 36,000 | <200 | 800 |
| Ac-W—Q—M—R—H—S—S$_s$ | 100,000 | <200 | <200 |
| Ac-W—Q—M—G—H—S—S$_s$ | 120,000 | <200 | <200 |

Antibody titres for each MAb were determined by ELISA and correspond to the reciprocal dilution of the ascites fluid giving an extinction of three times the test background. Values were corrected for non-specific absorption as determined by reacting each dilution of ascites fluid with unrelated peptide controls (Ac—G—D—L—G—S—I—S$_s$ and Ac—G—D—L—Q—V—L—S$_s$). Monoclonal antibodies tested were: Test MAb, anti-FMDV, type A$_{10}$ as described in the text (titre against the whole virus $1.3 \times 10^6$); anti-hepatitis A, site of reaction unknown (titre against hepatitis A virus $10^6$); and anti-myoglobin (sperm whale), site of reaction also unknown (titre against sperm whale myoglobin $10^6$).

EXAMPLE 2

Example 2 illustrates the application of the invention to a polyclonal antibody.

A further plurality of 8-catamers was synthesized with the general formula

Acetyl—NH—X—X—D$_2$—D$_1$—X—X—X—X—[-solid support]

as described in Example 1. This was tested against an antibody which had been produced against the synthetic peptide C—G—D—L—G—S—I—A—K. This peptide was prepared using the usual techniques of Merrifield solid-phase peptide synthesis. The peptide was coupled to Keyhole Limpet Haemocyanin through the sulfhydryl group of the cysteine moiety. The coupled peptide was formulated with Freund's incomplete adjuvant and injected into a rabbit via the intramuscular route. Antiserum was obtained by bleeding the rabbit 40 days after injection.

Figure 1:
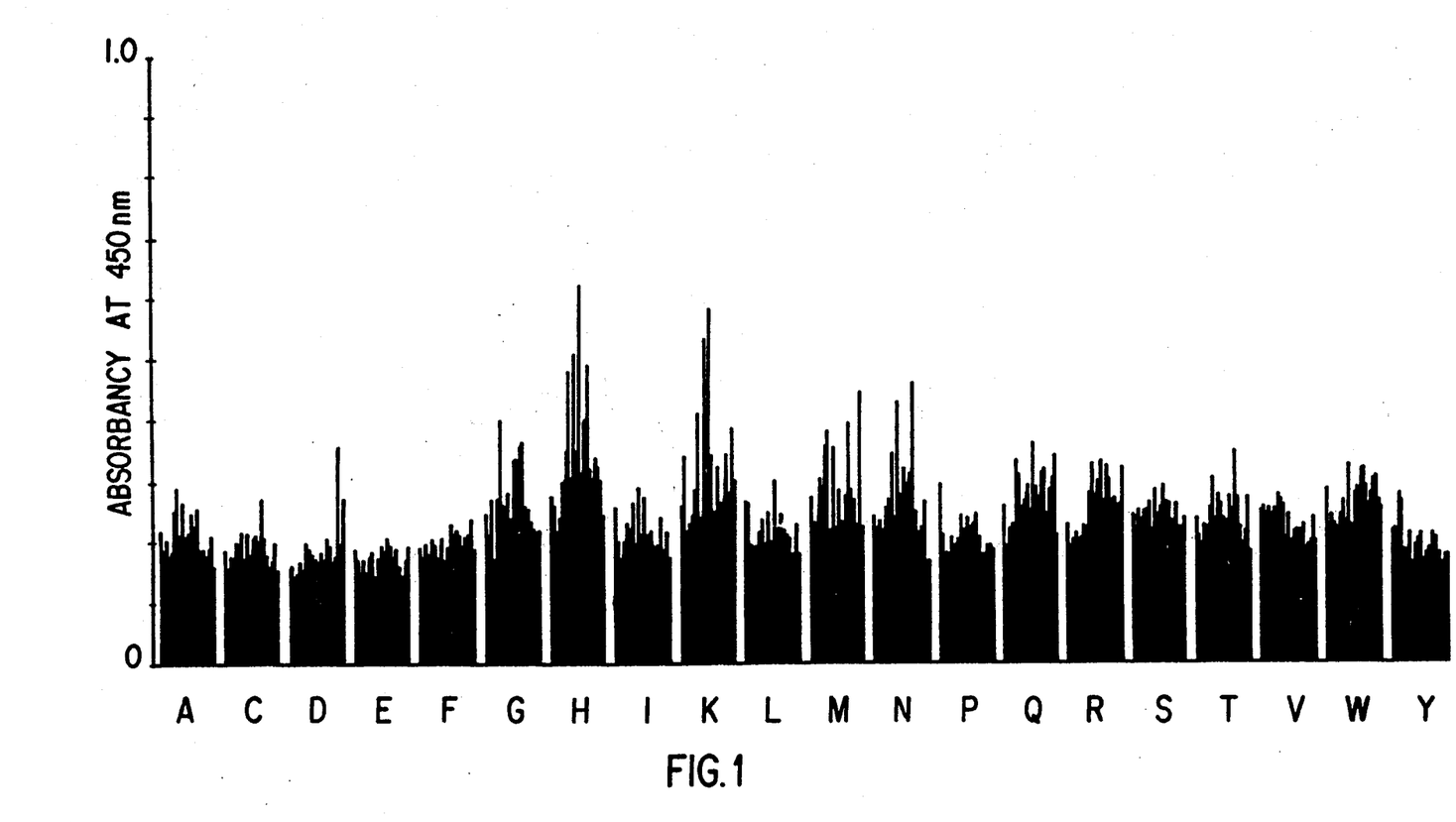
FIG. 1 shows the results of ELISA testing of 8-catamer preparations with monoclonal antibodies against FMDV.
Figure 3:
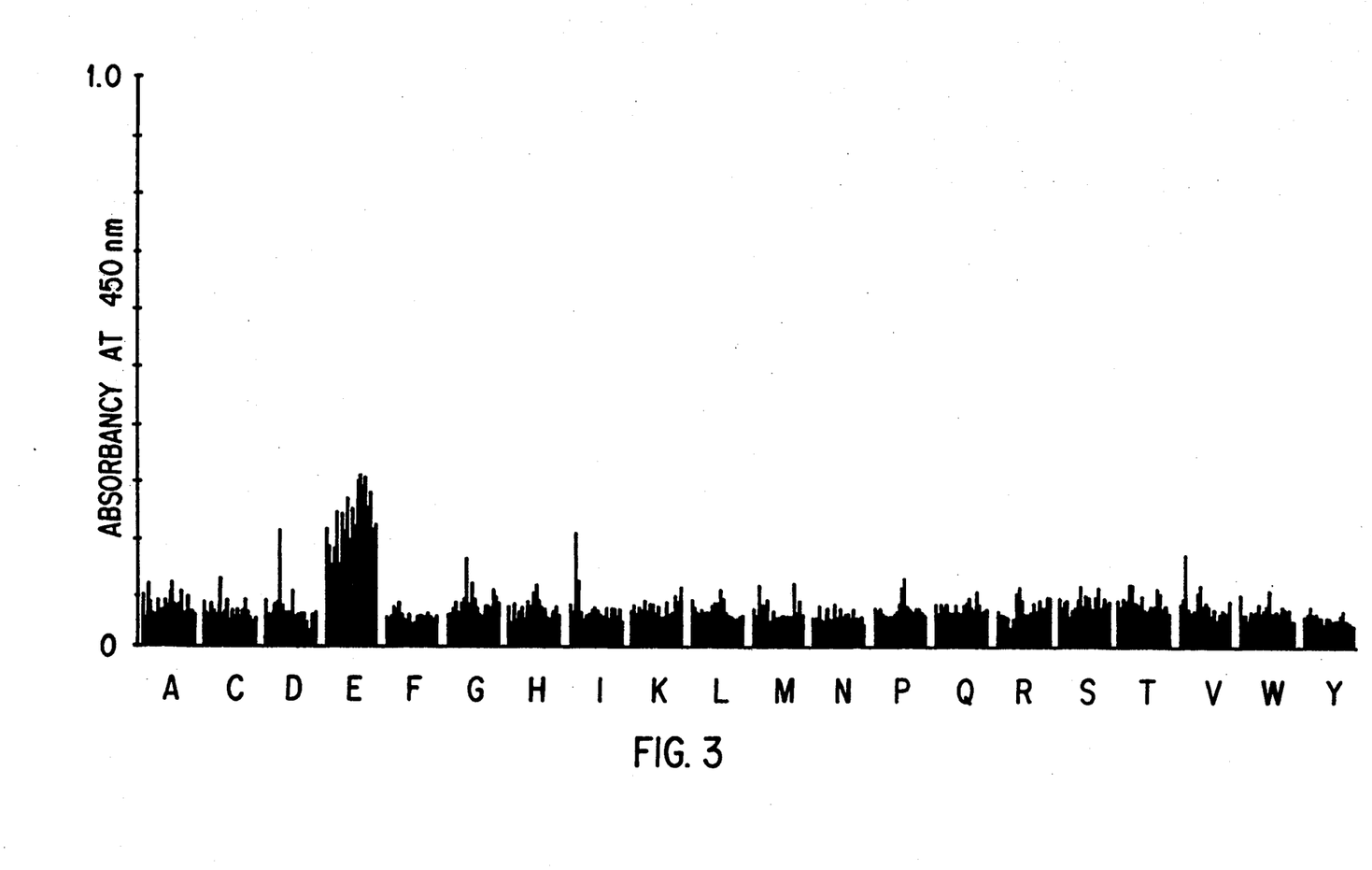
FIG. 3 shows the results of ELISA testing of 8-catamer preparations with monoclonal antibodies against the synthetic peptide C-G-D-L-G-S-I-A-K.
Figure 4A:
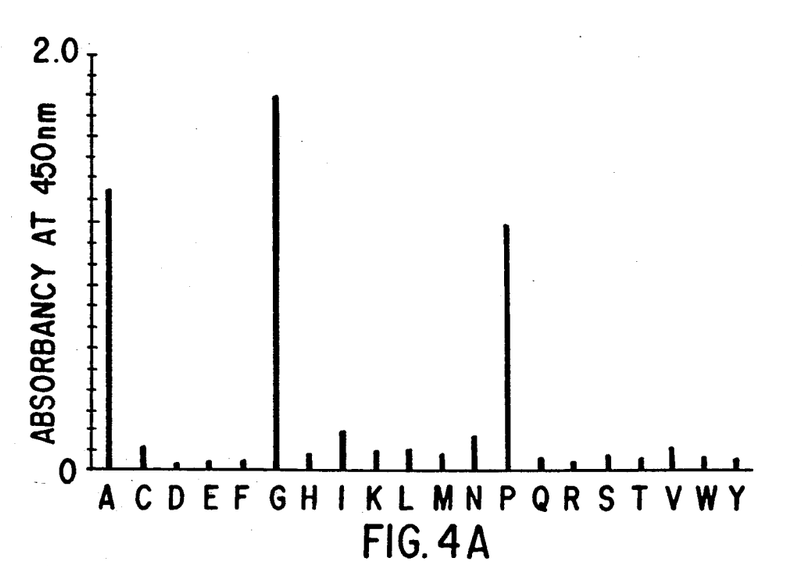
FIGS. 4A and 4B show the results of ELISA testing of 8-catamer preparations with monoclonal antibodies against the synthetic peptide C-G-D-L-G-S-I-A-K.
Figure 4B:
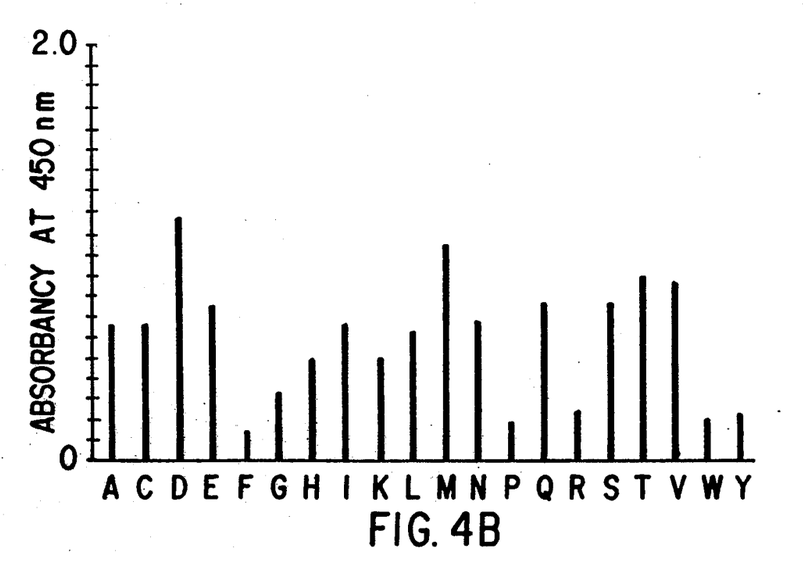
Figure 5:
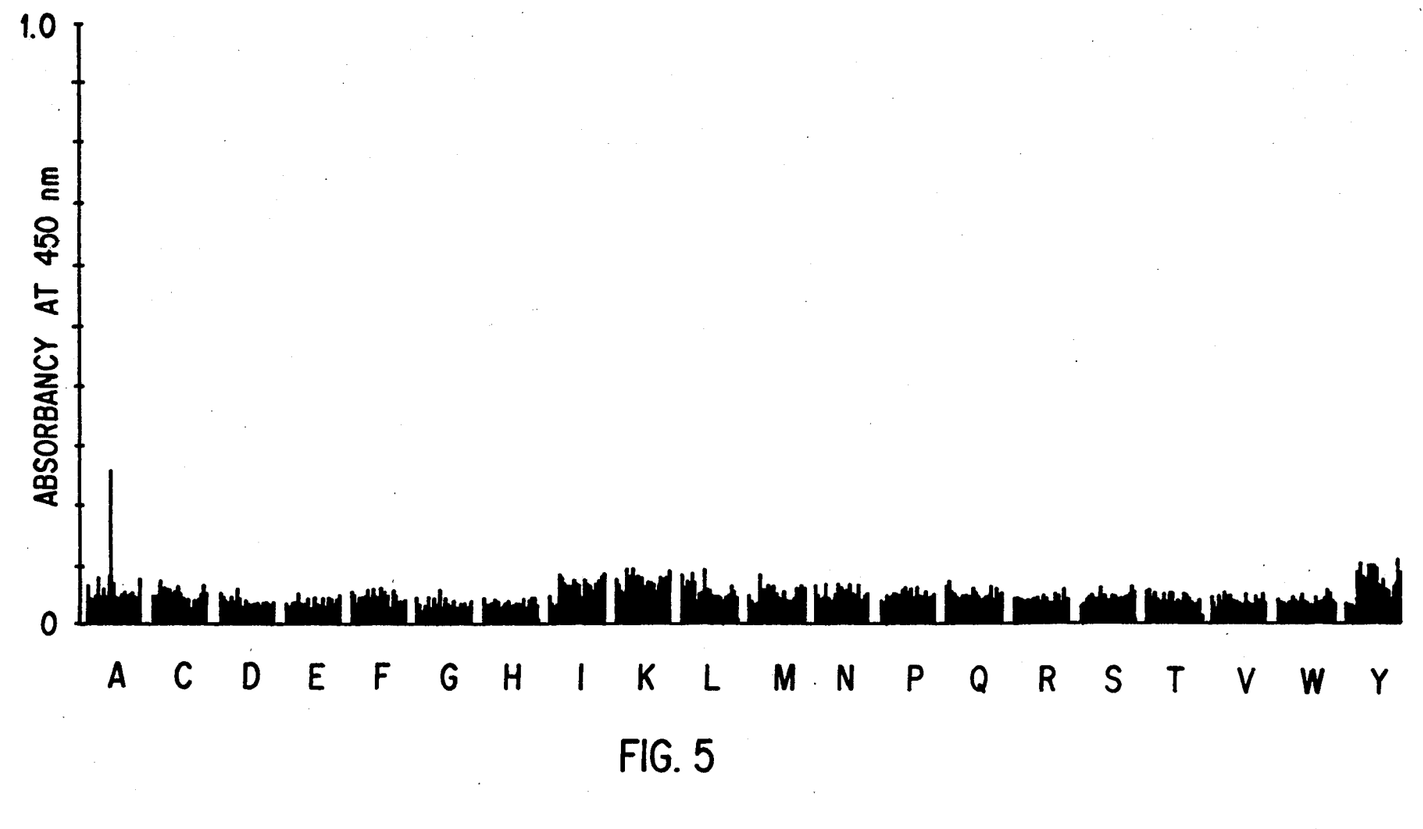
FIG. 5 shows the results of ELISA testing of 4-catamer preparations with monoclonal antibodies against sperm whale myoglobin.
Figure 6:
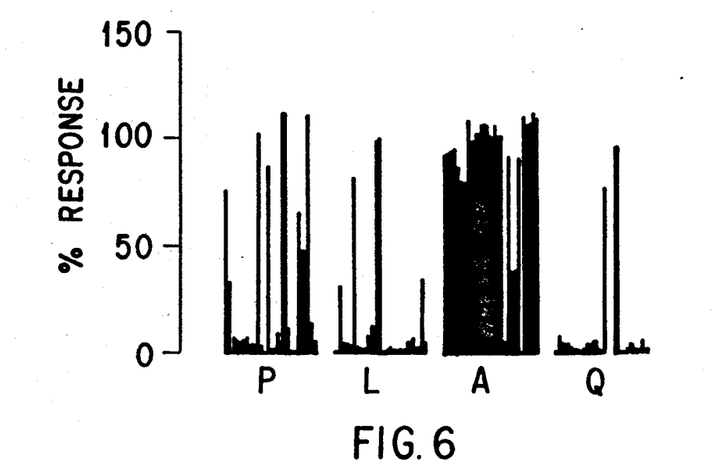
FIG. 6 shows the results of ELISA testing of 4-catamer preparations with monoclonal antibodies against sperm whale myoglobin.
Figure 7:
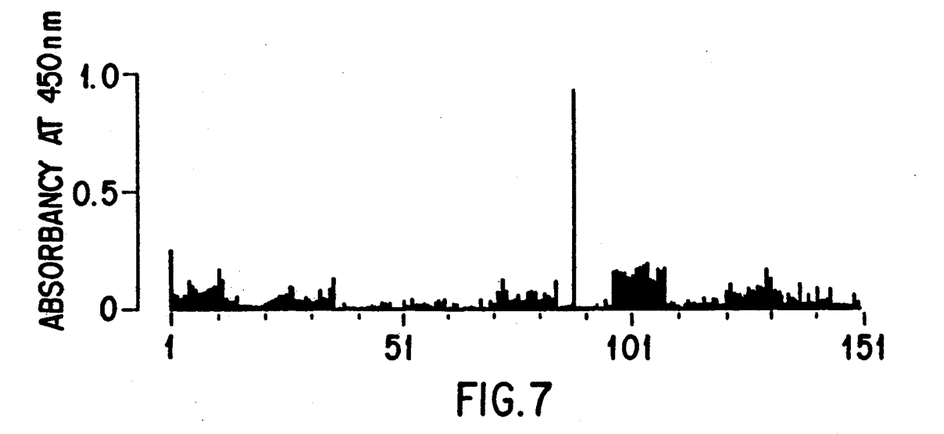
FIG. 7 shows the results of ELISA testing of 4-catamer preparations with monoclonal antibodies against sperm whale myoglobin.

The results of ELISA testing the plurality of 8-catamer preparations with the antibody are given in FIG. 3 in the same manner as in FIG. 1. It will be seen that all 8-catamer preparations which had E (glutamic acid) in the D$_1$ position reacted significantly with antibody. Other combinations which reacted significantly with antibody include in decreasing order: —D—I—, —G—D—, —I—G—, and —D—V—.

As described in Example 1 above, further pluralities of 8-catamer preparations were synthesized with the formulae:

Acetyl—NH—X—$D_3$—D—I—X—X—X—X—[solid support]

and

Acetyl—NH—X—X—D—I—$D_4$—X—X—X—[solid support]

where D is aspartic acid and I is isoleucine. Results of testing with the antibody are shown in FIG. 4 in the same manner as in FIG. 2. FIG. 4A represents 8-catamer preparations with the general formula Acetyl—NH—X—$D_3$—D—I—X—X—X—X—[solid support].

FIG. 4B represents 8-catamer preparations with the general formula

Acetyl—NH—X—X—D—I—$D_4$—X—X—X—[solid support].

FIG. 4 shows that 8-catamer preparations which react with antibody include the following sequences in the designated positions: —G—D—I—, —A—D—I—, —P—D—I—, —D—I—D—, —D—I—M— and —D—I—T—. It can plainly be seen by comparing FIG. 4A with FIG. 4B that the position immediately before the —D—I— pair permits far less latitude in allowable amino acids than does the position immediately after the —D—I— pair.

8-Catamer preparations based on the parent sequence

Acetyl—NH—X—X—G—D—I—D—X—X—[solid support]

were synthesized, in which at each of the four defined positions in the catamer preparation all 19 alternative amino acids were substituted, one at a time. Testing of this set of preparations for binding activity with the test antibody showed that to retain the ability to react with this antibody, the glycine residue could only be replaced with alanine; the amino-terminal aspartic acid could not be replaced by any amino acid; the isoleucine could be replaced with valine, leucine or threonine or with about ten other amino acids with a reduction of binding activity; and the carboxyl-terminal aspartic acid could be replaced by virtually any amino acid, serine in this position giving the strongest binding. The testing showed that the defined sequence G—D—I—S was the preferred one for extension.

Extending the defined sequence above demonstrated the preference for incorporation of tryptophan at the amino-terminal end and histidine at the carboxyl-terminal end. However, neither extension produced a very marked increase in the antibody-binding activity.

Further extension of the preferred defined sequence W—G—D—I—S—H showed that there was little advantage in extending the sequence further.

It will be noted that the mimotope determined for this particular antibody, namely, W—G—D—I—S—H has only a passing similarity to the peptide which was used to induce the antibody, namely, C—G—D—L—G—S—I—A—K. However, testing of the antibody in a replacement net based on the immunogenic sequence G—D—L—G—S—I showed a marked preference for the sequence G—D—L—G—D—I rather than the inducing sequence G—D—L—G—S—I ($E_{450}$ values 0.45 and 0.16 respectively). There is a similarity between the mimotope as determined and a preferred binding peptide for the antibody. This is strong evidence for the broad applicability of the method.

EXAMPLE 3

Example 3 illustrates that the length of the plurality of catamer preparations can be shorter than 8-catamers.

A plurality of 4-catamer preparations was synthesized with the general formula

Acetyl—NH—X—$D_2$—$D_1$—X—[solid support]

where the abbreviations are as used for Example 1. The method of synthesis was identical to that used for Example 1. This was tested against a monoclonal antibody which had been raised against sperm whale myoglobin using techniques well known to those skilled in the art.

The results of ELISA testing the plurality of 4-catamer preparations with the antibody are given in FIG. 5 in the same manner as in FIG. 1. It will be seen that only the catamer preparations with the formula Acetyl—NH—X—L—A—X—[solid support]

was able to react with the monoclonal antibody.

As described in Example 1 above, further pluralities of 4-catamer preparations were synthesized with the formulae:

Acetyl—NH—$D_3$—L—A—X—[solid support]

and

Acetyl—NH—X—L—A—$D_4$—[solid support]

Table 4 summarizes the most reactive catamer preparations when tested in an ELISA system with the monoclonal antibody.

TABLE 4

Relative antibody binding activities of 4-catamer preparations containing three defined amino acids.

| Amino-terminal extension | | Carboxyl-terminal extension | |
|---|---|---|---|
| Sequence | Activity | Sequence | Activity |
| AC—P—L—A—X—$S_s$ | 1.80 | Ac-X—L—A—Q—$S_s$ | 1.73 |
| Ac-A—L—A—X—$S_s$ | 1.36 | Ac-X—L—A—R—$S_s$ | 1.58 |
| Ac-F—L—A—X—$S_s$ | 1.33 | Ac-X—L—A—S—$S_s$ | 1.39 |
| Control sequences Ac-X—L—A—X—$S_s$ | | 1.00 ($E_{450}$ = 0.17) | |
| Ac-X—A—L—X—$S_s$ | | 0.94 | |

Catamer preparations based on the parent sequence

Acetyl—NH—P—L—A—Q—[solid support]

were synthesized to form a replacement net as described in Example 2. FIG. 6 shows the result of testing these peptides in an ELISA with the monoclonal antibody. Each group of twenty lines in FIG. 6 represents the response in percentage when compared to the mean of the parent response ($E_{450}$=2.62 with a background of 0.25). Each member of a group of twenty lines has had the amino acid indicated below substituted by another amino acid. The order of the lines is the alphabetical order of the single letter code of the amino acid. The thickened line in each group of twenty indicates the parent sequence P-L-A-Q. It can clearly be seen that for the catamer preparation to be able to bind to this monoclonal antibody with at least half the activity of the parent sequence the proline may be replaced with the valine, isoleucine, leucine, alanine or serine; the leucine can be replaced by phenylalanine only; the alanine is freely replaceable by virtually any other amino acid; and the glutamine residue can only be replaced by asparagine.

A set of all overlapping 4-catamers of the sperm whale myoglobin sequence was synthesized using the methods described for the designated positions in Example 1. These catamers were reacted in an ELISA with the monoclonal antibody The results are shown in FIG. 7. Each line represents the colour developed in an ELISA, read at 450 nm. Each line is numbered so that the residue at the amino terminal end of the particular catamer has the same number as in the sperm whale myoglobin sequence It can clearly be seen that the only 4-catamer which reacts with the monoclonal antibody is that comprising residues 88 to 91 of the sperm whale sequence. This sequence is P—L—A—Q. Clearly, the monoclonal antibody recognizes this particular determinant on the sperm whale myoglobin.

A set of 5-catamers with the general formulae

Acetyl—NH—$D_5$—P—L—A—Q—[solid support]

and

Acetyl—NH—P—L—A—Q—$D_6$—[solid support]

were synthesized to determine the best extensions to the defined sequence The best binding preparations were Acetyl—NH—K—P—L—A—Q—[solid support]

and

Acetyl—NH—P—L—A—Q—Y—[solid support].

It should be noted that the sequence K-P-L-A-Q is homologous with the sequence of sperm whale myoglobin at residues 87 to 91. Again, this example illustrates the applicability of this technique.

I claim:

1. A method of determining the sequences of amino acids which is a conformational equivalent of an epitope which is complementary to a particular paratope of an antibody of interest, the method comprising the steps of:

a. synthesizing a plurality of catamer preparations; each catamer having at least four positions; each of said catamer preparations consisting of a plurality of catamers made of a defined set of at least four amino acids and in which:

(i) a residue at two or more designated positions in each catamer are known and are constant for each catamer in the catamer preparation ("constant positions"), (ii) the residue at each of the remaining positions is randomly made up from members selected from said defined set of amino acids ("random positions"); wherein at least two of the positions of said catamer are random; and (iii) said plurality of catamer preparations comprising preparations in which the residue at the designated positions is systematically varied to contain members from said defined set of amino acids, wherein the number of catamers in said catamer preparation is the product of the number of amino acids selected for each random position;

b. contacting each of said plurality of catamer preparations with the antibody of interest;

c. detecting the presence or absence of binding between each of said plurality of catamer preparations and said given antibody;

d. determining a partial sequence of amino acids for the conformational equivalent of an epitope which is complementary to the particular paratope of said antibody from the known residue at two or more designated positions in each of said plurality of catamer preparations that bind to said antibody;

e. synthesizing a further plurality of catamer preparations as defined in step a and which include the composition of the partial sequence as determined in said step d as initial designation positions, each of said further plurality of catamer preparations having at least one additional position in each catamer as a designated position; and f. repeating steps b, c and d with said further plurality of catamer preparations.

2. A method according to claim 1, wherein each of said plurality of catamer preparations is made up from the set of alpha-amino acids.

3. A method according to claim 2, wherein each of said plurality of catamer preparations consists of a plurality of 4- to 8- catamers.

4. A method according to claim 1, wherein each of said plurality of catamers is synthesized on a solid support, and has the general formula:

Y—X—X—$D_2$—$D_1$—X—X—X—X—

Y—X—X—$D_2$—X—$D_1$—X—X—X— or $$Y-X-D_2-X-X-D_1-X-X-X-,$$

wherein Y is an end group of a catamer, X, which may be the same or different, is a member of a set of monomers such that each member is present in the catamer preparation, an $D_1$ and $D_2$ are known monomers which are constant in each of the catamer preparations.

5. A method according to claim 4, wherein each of said plurality of catamers has the general formula:

$$\text{Acetyl}-NH-X-X-D_2-D_1-X-X-X-X-$$

wherein X is a member of the set of L-alpha amino acids, and such plurality of catamers is such that each member of the set is present at the X position in approximately equi-molar amounts and $D_1$ and $D_2$ are selected from the set of L-alpha amino acids.

6. The method of claim 1 wherein each catamer has at least eight positions.

* * * * *